(12) United States Patent
Moser et al.

(10) Patent No.: US 8,740,991 B2
(45) Date of Patent: Jun. 3, 2014

(54) PROSTHETIC ANKLE JOINT MECHANISM

(71) Applicant: Blatchford Products Limited, Hampshire (GB)

(72) Inventors: David Moser, Hampshire (GB); Fadi Abimosleh, Springboro, OH (US); Mir Saeed Zahedi, London (GB); Graham Harris, Hampshire (GB); Stephen Terry Lang, Hampshire (GB); Andrew John Sykes, Surrey (GB)

(73) Assignee: Blatchford Products Limited, Hampshire (GB)

( * ) Notice: Subject to any disclaimer, the term of this patent is extended or adjusted under 35 U.S.C. 154(b) by 0 days.

(21) Appl. No.: 14/073,394

(22) Filed: Nov. 6, 2013

(65) Prior Publication Data
US 2014/0067086 A1    Mar. 6, 2014

Related U.S. Application Data

(63) Continuation of application No. 14/051,775, filed on Oct. 11, 2013, which is a continuation of application No. 11/956,391, filed on Dec. 14, 2007, now Pat. No. 8,574,312.

(60) Provisional application No. 60/869,959, filed on Dec. 14, 2006.

(51) Int. Cl.
*A61F 2/66* (2006.01)
*A61F 2/64* (2006.01)
*A61F 2/68* (2006.01)

(52) U.S. Cl.
USPC .................... 623/50; 623/47; 623/49; 623/53

(58) Field of Classification Search
CPC ..................................................... A61F 2/6007
USPC .......................................................... 623/50
See application file for complete search history.

(56) References Cited

U.S. PATENT DOCUMENTS

| 37,637 A | 2/1863 | Parmelee |
| 2,470,480 A * | 5/1949 | Fogg ................................ 623/26 |

(Continued)

FOREIGN PATENT DOCUMENTS

| CN | 101518473 A | 9/2009 |
| DE | 2 101 303 A1 | 6/1972 |

(Continued)

OTHER PUBLICATIONS

Hayes, W. C. et al.; "*Leg Motion Analysis During Gait by Multiaxial Accelerometry: Theoretical Foundations and Preliminary Validations*;" Journal of Biomechanical Engineeering, vol. 105 (1983) pp. 283-289.

(Continued)

*Primary Examiner* — David Isabell
*Assistant Examiner* — Jacqueline Woznicki
(74) *Attorney, Agent, or Firm* — Alston & Bird LLP (57) ABSTRACT

A prosthetic foot and ankle assembly includes a foot component and an ankle joint mounted thereto and having a fixed range of dorsi-plantar flexion. The ankle joint includes a joint mechanism in the form of a hydraulic linear piston and cylinder assembly having a pair of chambers on opposite sides of the piston to provide hydraulic damping continuously over the range of dorsi-plantar flexion. The joint mechanism further includes a valve arrangement controlling the flow of hydraulic fluid between the chambers. The valve arrangement includes first and second adjustable valves for independently controlling dorsi-flexion damping resistance and plantar-flexion damping resistance respectively. The joint mechanism includes a first flexion limiter that limits dorsi-flexion of the joint mechanism to a dorsi-flexion limit and a second flexion limiter that limits plantar-flexion of the joint mechanism to a plantar-flexion limit, thereby defining the fixed range of dorsi-plantar flexion.

9 Claims, 5 Drawing Sheets

(56) References Cited

U.S. PATENT DOCUMENTS

| | | | |
|---|---|---|---|
| 2,490,796 A * | 12/1949 | Gettman et al. | 623/26 |
| 2,541,234 A * | 2/1951 | Fulton | 188/282.1 |
| 2,657,393 A | 11/1953 | Haller | |
| 2,699,554 A | 1/1955 | Comelli | |
| 2,851,694 A | 9/1958 | Mario | |
| 3,871,032 A | 3/1975 | Karas | |
| 4,051,558 A | 10/1977 | Vallotton | |
| 5,030,239 A | 7/1991 | Copes | |
| 5,044,360 A | 9/1991 | Janke | |
| 5,116,383 A | 5/1992 | Shorter et al. | |
| 5,383,939 A | 1/1995 | James | |
| 5,458,656 A | 10/1995 | Phillips | |
| 5,913,901 A * | 6/1999 | Lacroix | 623/47 |
| 5,957,981 A | 9/1999 | Gramnas | |
| 6,033,440 A | 3/2000 | Schall et al. | |
| 6,080,197 A | 6/2000 | Chen | |
| 6,187,052 B1 | 2/2001 | Molino et al. | |
| 6,443,993 B1 | 9/2002 | Koniuk | |
| 6,517,585 B1 | 2/2003 | Zahedi et al. | |
| 6,863,695 B2 | 3/2005 | Doddroe et al. | |
| 7,611,542 B2 | 11/2009 | Bourne et al. | |
| 7,985,265 B2 | 7/2011 | Moser et al. | |
| 8,246,695 B2 | 8/2012 | Mosler | |
| 2002/0052663 A1 | 5/2002 | Herr et al. | |
| 2002/0082712 A1 | 6/2002 | Townsend et al. | |
| 2002/0120349 A1 | 8/2002 | Phillips | |
| 2002/0138153 A1 | 9/2002 | Koniuk | |
| 2004/0044417 A1 | 3/2004 | Gramnas | |
| 2004/0054423 A1 | 3/2004 | Martin | |
| 2004/0236435 A1 | 11/2004 | Chen | |
| 2005/0109563 A1 | 5/2005 | Vitale et al. | |
| 2005/0192677 A1 | 9/2005 | Ragnarsdottir et al. | |
| 2005/0267601 A1 | 12/2005 | Chen | |
| 2006/0069448 A1 | 3/2006 | Yasui | |
| 2006/0069449 A1 | 3/2006 | Bisbee et al. | |
| 2006/0235544 A1 | 10/2006 | Iversen et al. | |
| 2006/0249315 A1 | 11/2006 | Herr et al. | |
| 2007/0043449 A1 | 2/2007 | Herr et al. | |
| 2008/0004718 A1 | 1/2008 | Mosler | |
| 2008/0262635 A1 | 10/2008 | Moser et al. | |
| 2008/0281435 A1 | 11/2008 | Abimosleh et al. | |
| 2008/0300692 A1 | 12/2008 | Moser et al. | |
| 2008/0306612 A1 | 12/2008 | Mosler | |
| 2012/0130508 A1 | 5/2012 | Harris et al. | |

FOREIGN PATENT DOCUMENTS

| | | |
|---|---|---|
| EP | 0 549 855 B1 | 3/1996 |
| EP | 0 948 947 A2 | 10/1999 |
| EP | 1 068 844 A1 | 1/2001 |
| GB | 643734 A | 9/1950 |
| GB | 2 234 907 A | 2/1991 |
| GB | 2 305 363 | 4/1997 |
| GB | 2 328 160 A | 2/1999 |
| JP | 59-183747 A | 10/1984 |
| JP | 59-189843 A | 10/1984 |
| JP | 2001-514925 A | 9/2001 |
| JP | 2004-506480 A | 3/2004 |
| JP | 2008-536614 T | 9/2008 |
| JP | 2009-515628 A | 4/2009 |
| WO | WO 93/06795 A1 | 4/1993 |
| WO | WO 96/25898 A1 | 8/1996 |
| WO | WO 99/00075 A1 | 1/1999 |
| WO | WO 00/76429 A1 | 12/2000 |
| WO | WO 02/15826 A1 | 2/2002 |
| WO | WO 03/086245 A2 | 10/2003 |
| WO | WO 2006/112774 A1 | 10/2006 |
| WO | WO 2007/027808 A2 | 3/2007 |
| WO | WO 2007/054736 A2 | 5/2007 |
| WO | WO 2008/071975 A1 | 6/2008 |
| WO | WO 2008/103917 A1 | 8/2008 |

OTHER PUBLICATIONS

Morris, J.W.; "*Accelerometry—A Technique for the Measurement of Human Body Movements*;" Journal of Biomechanics (1973) pp. 726-736.

Anatomic and Biomechanical Characteristics of the Ankle Joint and Total Ankle Arthroplasty, Total Ankle Arthroplasty, Dec. 5, 2005, Springer Vienna, ISBN 978-3-211-21252 (print) 978-3-211-27254-1 (online), pp. 25-42.

Combined Search and Examination Report for Great Britain Application No. GB1201875.0 dated Apr. 12, 2012.

Endolite Global—Echelon VT Foot—Prescription [online][retrieved May 7, 2012]. Retrieved from the Internet: <URL: http://www.endolite.co.uk/products/feet/echelon_vt/echelon_vt_foot.html> 1 page.

Hydraulik Ankle Unit Manual; Mauch Laboratories, Inc.; Mar. 1988.

International Search Report and Written Opinion for International Application No. PCT/US2008/054741, mailed Jul. 2, 2008.

International Search Report and Written Opinion for International Application No. PCT/GB2012/000112, mailed May 5, 2012.

Office Action for Japanese Application No. 2009-551033 dated Sep. 11, 2012.

Office Action for U.S. Appl. No. 11/956,391; dated Jul. 30, 2013.

Office Action for U.S. Appl. No. 13/150,694; dated Dec. 14, 2012.

Office Action for U.S. Appl. No. 13/364,786, dated May 22, 2013.

Search Report for Great Britain Application No. 1101893.4 dated May 11, 2011.

Segal, et al.; "*Kinematic Comparisons of Transfemoral Amputee Gait Using C-Leg and Mauch SNS Prosthetic Knees;*" The Journal of Rehabilitation Research and Development, vol. 43, No. 7; pp. 857-879; dated Nov./Dec. 2006; Figure 3.

Office Action for U.S. Appl. No. 11/956,391; dated Sep. 18, 2009.

Office Action for U.S. Appl. No. 11/956,391; dated May 10, 2011.

Office Action for U.S. Appl. No. 12/035,717; dated Aug. 5, 2009.

Office Action for U.S. Appl. No. 13/150,694; dated Jul. 19, 2013.

* cited by examiner

PROSTHETIC ANKLE JOINT MECHANISM

CROSS-REFERENCE TO RELATED APPLICATION

The present application is a continuation of U.S. application Ser. No. 14/051,775, filed Oct. 11, 2013, which is a continuation of U.S. application Ser. No. 11/956,391, filed Dec. 14, 2007, which claims the benefit of U.S. Provisional Application No. 60/869,959 filed Dec. 14, 2006, the entire disclosures of which are hereby incorporated herein by reference.

BACKGROUND OF THE INVENTION

This invention relates to a prosthetic ankle joint mechanism, to a lower limb prosthesis comprising a shin component, a foot component, and a joint mechanism interconnecting the shin and foot components, and to a prosthetic foot and ankle assembly. The joint mechanism is arranged to allow limited damped pivoting movement of the shin component relative to the foot component.

Current prosthetic foot and ankle systems are generally aligned for operation as fixed mechanical structures comprising elastic and deformable elements designed to provide stability during standing and walking and to return energy for propulsion into the swing phase of the walking cycle. However, such a device is often uncomfortable for the user whilst standing and whilst walking on ramps and stairs and walking at different speeds. Users have also experienced knee instability and difficulty in maintaining forward motion during roll-over of the foot while standing and walking on ramps and stairs, with consequent impairment of efficiency. These difficulties are particularly important for transfemoral amputees whose stance phase action is normally compromised by significantly reduced knee flexion and extension which would otherwise assist shock absorption and forwards propulsion during the stance phase.

An ankle joint mechanism allowing dynamic hydraulic control of the angular position of a prosthetic foot with respect to a shin component is disclosed in Mauch Laboratories, Inc., Hydraulik Ankle Unit Manual, March 1988. The shin component is attached to a vane piston housed in a fluid-filled chamber with a concave part-circular lower wall. A gravity-controlled ball rolls forwards and backwards on the wall according to the orientation of the foot to open or close a bypass passage in the piston. As a result, dorsi-flexion of the mechanism is prevented when the shin component is vertical, largely irrespective of whether the foot is horizontal or inclined downwardly or upwardly. Such a prosthesis also suffers partly from the disadvantages described above.

Amongst other known prosthetic ankle systems is that of U.S. Pat. No. 3,871,032 (Karas). This system contains a damping device having a dual piston and cylinder assembly with tappet return springs acting continuously to return the ankle to a neutral position. EP-A-0948947 (O'Byrne) discloses a prosthetic ankle having a ball-and-socket joint with a chamber filled with a silicone-based hydraulic substance, the joint having a visco-elastic response. In one embodiment, the chamber contains solid silicone rubber particles suspended in a silicone fluid matrix. US2004/0236435 (Chen) discloses a hydraulic ankle arrangement with adjustable hydraulic damping and resilient biasing members mounted anteriorly and posteriorly of an ankle joint rotation axis. In WO00/76429 (Gramtec), a leg prosthesis is described having an ankle joint allowing heel height adjustment by way of a hydraulic piston and linkage arrangement. Elastic components absorb shock during walking. US2006l0235544 (Iversen et al) discloses a hydraulic ankle mechanism with a rotary vane.

BRIEF SUMMARY OF THE INVENTION

According to a first aspect of this invention, a prosthetic ankle joint mechanism provides a continuously hydraulically damped range of ankle flexion, the mechanism being constructed and arranged such that, over at least part of said range, the damping resistance is the predominant resistance to flexion. The mechanism preferably comprises a hydraulic linear piston and cylinder assembly. The piston may have distal connection means for pivotal connection to a foot component, the cylinder having proximal connection means for connection to a shin component. Typically, the piston and cylinder assembly has a central axis which is oriented such that when the mechanism is coupled to a prosthetic shin component, the central axis is substantially aligned with or parallel to a shin axis defined by the shin component.

To allow individual setting of dorsi and plantar-flexion damping resistances, the mechanism may have a valve arrangement controlling the flow of hydraulic fluid between chambers of the piston and cylinder on opposite sides of the piston, the valve arrangement preferably comprising first and second adjustable valves for dorsi-flexion and plantar flexion damping control respectively.

According to another aspect of the invention, a prosthetic ankle joint mechanism provides a continuously hydraulically damped range of ankle flexion, the mechanism being constructed and arranged such that, over at least part of the range, movement in the dorsi and plantar directions is substantially unbiased resiliently.

The invention also includes a prosthetic foot and ankle assembly comprising the combination of a foot component and, mounted to the foot component, an ankle joint mechanism having the features described above. It is preferred that the ankle joint mechanism includes flexion limiting means limiting dorsi flexion of the joint mechanism to a dorsi-flexion limit, the shin connection interface being arranged to allow connection of a shin component at different anterior-posterior tilt angles. These angles include angles resulting in the shin component having an anterior tilt of at least 3° with respect to the vertical when the joint mechanism is flexed to the dorsi-flexion limit. The dorsi-flexion limit advantageously corresponds to a predetermined orientation of the shin component interface relative to the foot component and may be defined by a mechanical end stop operative by the abutment of one part of the prosthetic foot and ankle assembly associated with the shin component interface against another part of the assembly associated with the foot component. Conveniently, the end stop is defined by the piston of the piston and cylinder assembly abutting an end wall of the cylinder.

In the preferred embodiment of the invention described hereinafter, the range of damped ankle flexion is fixed. Nevertheless, the above-mentioned dorsi-flexion limit may be adjustable over at least a range of anterior-posterior tilt angles from 3° to 6°. In another embodiment, the range of damped flexion may alter when the dorsi-flexion limit is adjusted, but once the adjustment has been made, the range of damped flexion is, likewise, fixed from step to step.

The assembly may be arranged such that the relative position of the foot component and the shin connection interface at the dorsi-flexion limit is defined independently of the orientation of the assembly in space.

Adjustment of the shin axis orientation in the anterior-posterior direction with respect to the foot component may be performed using at least one conventional pyramid alignment interface, preferably the shin component interface.

The above-described prosthesis, in which the ankle allows dorsi-plantar flexion over a limited range of movement with largely damped, as opposed to resilient, resistance to motion results in an ankle which is able easily to flex under load according to changing activity requirements without generation of high reaction moments which would otherwise cause discomfort and compromise the function of the prosthesis. Providing damped and substantially unbiased movement means that the ankle thereby functions in a way such that it remains in its last loaded orientation, having no re-alignment capability once the foot is unloaded. This feature is advantageous to assist foot clearance during the swing phase.

By arranging for the position of the foot component or the foot component interface relative to the shin connection interface at the dorsi-flexion limit to be defined independently of the orientation of the assembly in space, and by using gravity-independent determination of the dorsi-flexion limit, the need for a gravity-dependent valve system with an end-stop corresponding to vertical orientation of the shin axis is avoided. The prosthesis described above allows set-up flexibility to alter the dynamics of roll-over through selection of different toe spring stiffnesses. The range of yielding motion can be altered by altering the relative alignment of the foot and shin components. Allowing the shin axis to move to the anterior of the vertical position is particularly advantageous during stair and ramp walking activities.

The conventional approach of maximising energy storage and return has produced designs in which the ankle has a high elastic stiffness at all times. Reducing stiffness in the manner proposed in accordance with the present invention greatly improves comfort for the user as well as helping to preserve forwards momentum of the upper body and thus locomotion efficiency. Reaction moments about the ankle are largely dissipated with the result that voluntary control and proprioception of the knee and hip in BK (below-knee) amputees, in particular, is improved.

According to a further aspect of the invention, there is provided a prosthetic foot and ankle assembly comprising the combination of an ankle joint mechanism as described above, together with a prosthetic energy-storing foot which is resiliently deformable to allow dorsi-flexion of at least an anterior portion of the foot relative to an ankle-mounting portion of the foot.

The invention also includes a lower limb prosthesis comprising a shin component defining a shin axis, a foot component, and an ankle joint mechanism as described above, the ankle joint mechanism coupling the shin component to the foot component, wherein at least one of the foot component and the shin component includes a resilient section allowing resilient dorsi-flexion of at least an anterior portion of the foot component relative to the shin axis. The foot component may comprise an energy-storing spring arranged to be deflected when a dorsi-flexion load is applied to the foot anterior portion. Alternatively, the prosthesis may include a resilient section associated with the coupling of the foot component and the ankle joint mechanism, allowing a degree of resilient dorsi-flexion. As another alternative, there may be a resilient section associated with the coupling of the shin component to the ankle joint mechanism.

Another aspect of the invention resides in a prosthetic foot and ankle assembly comprising the combination of an ankle joint mechanism and a prosthetic foot having an anterior portion, a posterior portion and an ankle-mounting portion, wherein the assembly constitutes a Maxwell-model damper/spring combination of which the damper element is said ankle joint mechanism and the spring element is a spring component arranged in series with the ankle joint.

Described below is a lower limb prosthesis comprising a shin component defining a shin axis, a foot component, and a joint mechanism interconnecting the shin and foot components and arranged to allow limited damped pivoting of the shin component relative to the foot component about a medial-lateral joint flexion axis during use, wherein the mechanism comprises: a piston and cylinder assembly the piston of which is movable so as define a variable-volume fluid-filled chamber of the assembly, fluid being admitted to or expelled from the chamber through at least one damping orifice as the relative orientation of the shin and foot components varies with flexion of the joint mechanism; and flexion limiting means limiting dorsi-flexion of the joint mechanism to a dorsi-flexion limit corresponding to orientation of the shin component with the shin axis tilted anteriorly with respect to the vertical by at least 3 degrees. The joint mechanism is preferably arranged such that damped relative pivoting of the shin component and the foot component is allowed over an angular range between dorsi- and plantar-flexion limits, the dorsi-flexion limit being adjustable to different anterior tilt settings of the shin axis with respect to the foot component. In particular, the angular range encompasses a foot-flat, shin-axis-vertical state with the permitted degree of shin axis tilt being adjustable to different values to the anterior of the vertical.

In the preferred embodiment of the invention, the joint mechanism has a first part associated with the shin component and a second part associated with the foot component, these two parts being pivotally interconnected with the connection defining a joint flexion axis. One of the two parts includes the chamber of the piston and cylinder assembly and the other is pivotally connected to the piston, the mechanism being arranged such that the dorsi-flexion limit is defined by a mechanical stop limiting relative rotation of the first and second parts. This mechanical stop may be the abutment of the piston with an end surface of the chamber. A cushioning spring or pad may be applied to the top surface of the piston or to the opposing chamber surface in order to increase the resistance to dorsi-flexion as the dorsi-flexion limit is approached.

As for the ability to preset the dorsi-flexion limit, this may be facilitated in a number of ways. For instance, the limit may be set by an adjustable anterior-posterior tilt alignment interface, typically between the joint mechanism and a shin component such as a shin tube. The interface may be of the well-known inverted pyramid construction as described above. Alternatively, the interface may be provided between the joint mechanism and a foot component. Again this may be of inverted-pyramid construction. Another possibility is a lockable pivot joint for connecting the foot component to the joint mechanism, having an adjustment axis running in the medial-lateral direction. As a further alternative, an adjustable end stop may be provided in the piston and cylinder assembly, or the connection between the piston and one of the components of the mechanism mounting the foot component or the shin component may be adjustable to alter the range of displacement of the piston in the chamber of the assembly with respect to the angular range of movement of the foot component relative to the shin component.

The preferred joint mechanism includes two passages in communication with the above-mentioned chamber of the piston and cylinder assembly, each containing a respective non-return valve, one oriented to prevent the flow of fluid from the chamber through its respective passage and the other oriented to prevent the admission of fluid to the chamber through the other passage, so that one permits fluid flow when the joint mechanism is flexing in the direction of dorsi-flexion while the other passage permits the flow of fluid when the joint is flexing in the direction of plantar-flexion. Preferably, both passages have respective adjustable-area damping orifices to allow the degree of damping to be tuned to the user's requirements.

It is preferred that the piston and cylinder assembly is a hydraulic piston and cylinder assembly, although it is possible to use a pneumatic assembly.

A locking device may also be provided for locking the joint mechanism against pivoting at any of a number of positions of the foot component relative to the shin component. Typically this is performed using a manually or electromechanically operated valve which interrupts the flow of fluid to or from the above-mentioned chamber of the piston and cylinder assembly through the bypass passages. The locking device comprises a control member having two positions, one in which the joint mechanism operates in a yielding mode and one in which it operates in a locked mode. Retaining means are provided for retaining the control member in either of the two positions, e.g. a spring biasing the control member into one position and a detent, latch or lock for keeping the control member in the other position.

The invention also includes a prosthetic ankle unit comprising a foot connection interface, a shin connection interface pivotally connected to the foot connection interface to allow flexion of the unit, a piston and cylinder assembly having a piston that is movable in a fluid-filled chamber of the assembly, the piston being associated with one of the interfaces and the chamber with the other so that when the shin connection interface pivots relative to the foot connection interface, the piston moves in the chamber, fluid being admitted to or expelled from the chamber through at least one damping orifice according to the direction of flexion of the unit, wherein the unit further comprises flexion limiting means limiting dorsi-flexion of the unit to a dorsi-flexion limit corresponding to a selected angular position of the interfaces relative to each other, and wherein at least one of the connection interfaces is configured to allow anterior-posterior tilt adjustment.

The invention will be described below by way of example with reference to the drawings.

DETAILED DESCRIPTION OF THE DRAWINGS

Figure 1:
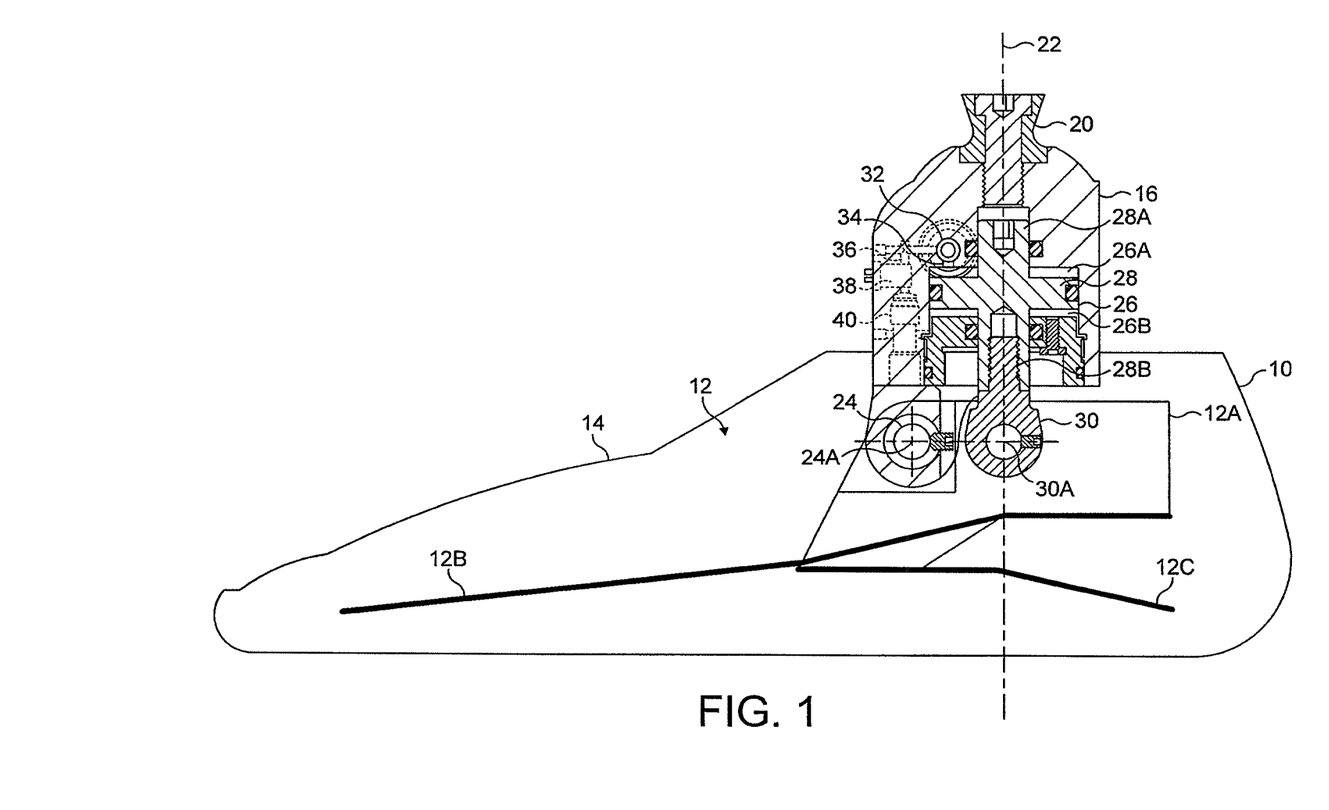
FIG. 1 is a cross-section of a foot-ankle prosthesis in accordance with the invention, including a first ankle unit, sectioned on a central anterior-posterior (AP) plane.

Referring to FIG. 1, an foot-ankle prosthesis in accordance with the invention has a foot component 10 with a foot keel 12 comprising a rigid carrier 12A, and a toe spring 12B and a heel spring 12C which are independently coupled to the carrier 12A. The keel 12 is a one-piece component made from a carbon fibre composite material and is surrounded by a foam cosmetic covering 14.

Mounted to the foot keel 12 is an ankle unit 16 comprising a joint mechanism 18 and a shin connection interface 20. The shin connection interface 20 defines a shin connection axis 22. The mounting of the ankle unit 16 to the foot keel 12 is by way of an ankle flexion pivot 24 defining a flexion axis 24A running in a medial-lateral direction to the anterior of the shin connection axis 22.

The body of the ankle unit 16 forms the cylinder of a piston and cylinder assembly having a piston 28 with upper and lower piston rods 28A, 28B, the lower piston rod being pivotally connected to the foot keel 12 at a second pivotal connection 30, this second pivotal connection defining a second medial-lateral axis which is spaced, in this case posteriorly, from the flexion axis 24A. It will be seen that as the body 16 of the ankle unit pivots about the flexion axis 24A, the piston 28 moves substantially linearly in the cylinder 26.

The cylinder 26 of the piston and cylinder assembly is divided into upper and lower chambers 26A, 26B. These chambers are linked by two bypass passages in the ankle unit body 16, one of which is visible in FIG. 1 where it is shown by dotted lines since it is behind the sectioning plane of the drawing. The other passage does not appear in FIG. 1 since it is located in front of the sectioning plane. However, its configuration is almost identical, as will be described below. These two bypass passages communicate with the upper chamber 26A of the cylinder via a locking valve 32, described in more detail below, and a common linking passage 34 which opens into the upper chamber 26A.

The two bypass passages, one of which, 36, is shown in FIG. 1, each contain a damping resistance control valve constituting a manually adjustable area orifice 38 and a non-return valve 40. This adjustable-area orifice and the non-return valve 40 are arranged in series in the bypass passage 36 between the locking valve 32 and the lower chamber 26B.

The bypass passage 36 appearing in FIG. 1 has its non-return valve 40 oriented to allow the flow of hydraulic fluid from the lower chamber 26B to the upper chamber 26A. The other bypass passage (not shown) has its non-return valve oriented in the opposite direction. Accordingly, one of the passages 36 is operative during dorsi-flexion and the other during plantar-flexion. When the locking valve 32 is open, continuous yielding movement of the foot component 10 relative to the ankle unit 16 about the flexion axis 24A is possible between dorsi-flexion and plantar-flexion limits defined by the abutment of the piston with, respectively, the lower wall and the upper wall of the cylinder 26. The level of damping for dorsi-flexion and plantar-flexion is independently and manually presetable by the respective adjustable-area orifices.

The shin connection interface 20 is conventional, being of pyramid construction. Typically, a tubular shin component is mounted to the shin connection interface 20, the shin component having, at its distal end, an annular female pyramid receptacle having alignment screws, as well known to those skilled in the art, for adjusting the orientation of the shin component relative to the ankle unit 16. At a neutral alignment position, the axis of the shin component (the shin axis) is coincident with the shin connection axis 22 (shown in FIG. 1). When the shin component is affixed to the ankle unit 16 in this neutral position, the limit of dorsi-flexion of the ankle-foot prosthesis, defined by the abutment of the piston 28 with the lower wall of the cylinder 26 corresponds to an anterior tilt of the shin axis relative to the vertical when the user stands on a horizontal surface. The plantar flexion limit, defined by abutment of the piston 28 with the upper wall of the cylinder 26 corresponds to a posterior tilt of the shin axis.

In this embodiment, the anterior and posterior tilt angles of the shin connection axis 22 at the dorsi-flexion and plantar-flexion limits are 4 degrees (anterior) and 8 degrees (posterior) respectively with respect to the vertical.

In this embodiment, the mechanical end-stops represented by the abutment of the piston 28 with the lower and upper cylinder walls define a yield range over which the ankle-foot prosthesis is free to flex during locomotion and during standing, providing the locking valve 32 is open. Alteration of the shin component alignment at the shin connection interface 20 does not alter the angular magnitude of the yielding range because it is governed by the piston stroke, but it does alter the position of the limits with respect to the vertical.

It will be understood, therefore, that the angular range magnitude is fixed by the construction and geometry of the ankle-foot prosthesis and its hydraulic joint mechanism. The degrees of dorsi-flexion and plantar-flexion respectively are altered by the alignment of the shin component connection, as described above. It will be understood that alternative alignment interfaces can be used to adjust the positions of the dorsi-flexion and plantar-flexion limits. For instance, an anterior-posterior tilt alignment interface may be provided between the ankle unit 16 and the foot keel 12. Such an interface is provided by a second embodiment of the invention, as will now be described with reference to FIGS. 2 and 3.

Figure 2:
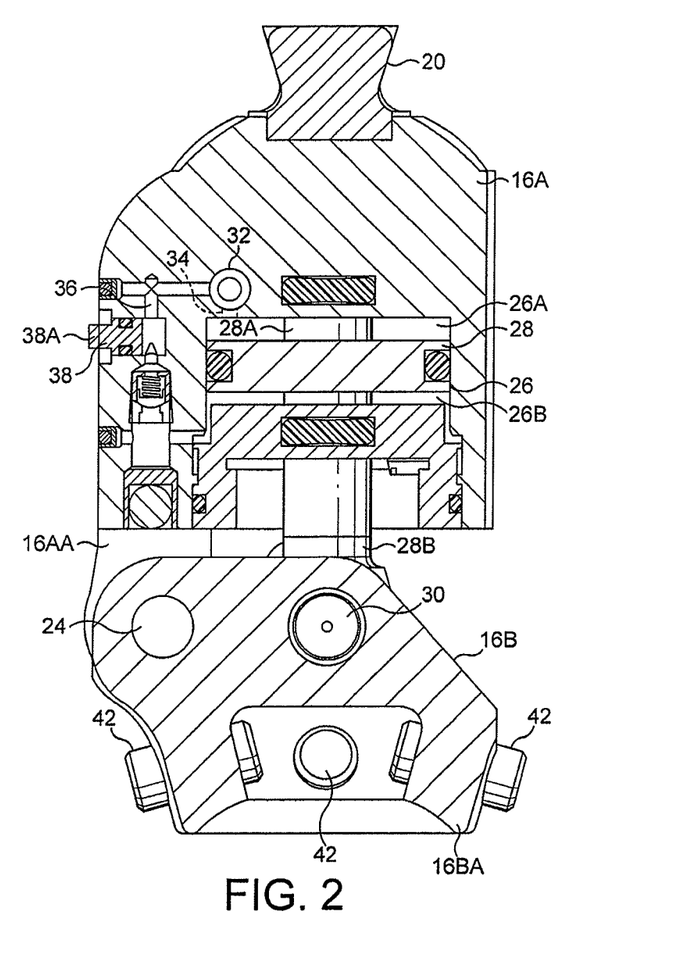
FIG. 2 is a cross-section of an alternative ankle unit for use in a prosthesis in accordance with the invention, sectioned on an AP in front of the central AP plane.

Referring to FIG. 2, this second embodiment of the invention takes the form of a two-part ankle unit having an ankle unit body 16A which, as before, mounts a shin connection interface 20 for adjustable connection to a shin component (not shown), and a foot mounting component 16B which incorporates a foot connection interface for receiving a pyramid connector of the known kind on a foot keel (not shown). The joint mechanism is identical to that described above with reference to FIG. 1 with the exception that the flexion and piston rod connection pivots 24, 30 are housed in the foot mounting component 16B rather than directly in the keel of a prosthetic foot. In the case of FIG. 2, the drawing is a cross-section on a vertical anterior-posterior plane parallel to but spaced from the axis of the shin connection interface 20 and the cylinder 26. Consequently, the bypass passage permitting hydraulic fluid flow from the lower chamber 26B to the upper chamber 26A of the cylinder 26 (corresponding to dorsi-flexion, i.e. clockwise rotation of the foot mounting component 16B relative to the ankle unit body 16A about the pivot 24) appears in full lines, whereas the common linking passage 34 between the control valve 32 and the upper chamber 26A is shown with dotted lines.

It will be understood that the non-return valve 40 has a counterpart non-return valve in the bypass passage (not shown) allowing for plantar flexion, but that the orientation of that counterpart valve is reversed from that shown in FIG. 2, as described above with reference to FIG. 1.

For the avoidance of doubt, it should be pointed out that the bores in the ankle unit body 16A which house the upper and lower piston rods 28A, 28B provide sufficient clearance around the piston rods to allow a limited degree of rocking of the piston 28 and piston rods 28A, 28B relative to the cylinder as the foot mounting component 16B rotates with respect to the ankle unit body 16A. The periphery of the piston 28 is shaped so as to have an arcuate cross-section, also for this reason. The same features are present in the ankle unit of FIG. 1.

The distal part of the ankle unit body 16A is in the form of a trunnion 16AA housing pivot axles of the flexion pivot 24 and the piston rod connection pivot 30. The foot mounting component 16B has an integral annular female pyramid alignment coupling 16BA. This annular pyramid connector includes four screws 42, three of which are shown in FIG. 2.

Figure 3:
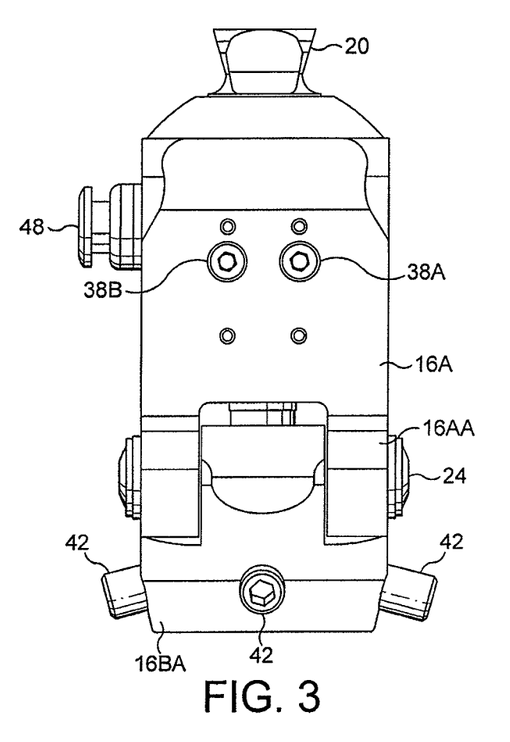
FIG. 3 is an anterior elevation of the ankle unit of FIG. 2.

The ankle unit trunnion 16AA is shown more clearly in FIG. 3. Also visible in FIG. 3 are two adjustment screws 38A, 38B which are accessible on the anterior face of the ankle unit body 16A. These form part of the adjustable-area orifices or flow resistance adjusters, one of which appears as valve 38 in FIG. 2, and permit manual adjustment of damping resistance in the dorsi- and plantar-flexion directions respectively.

Figure 4:
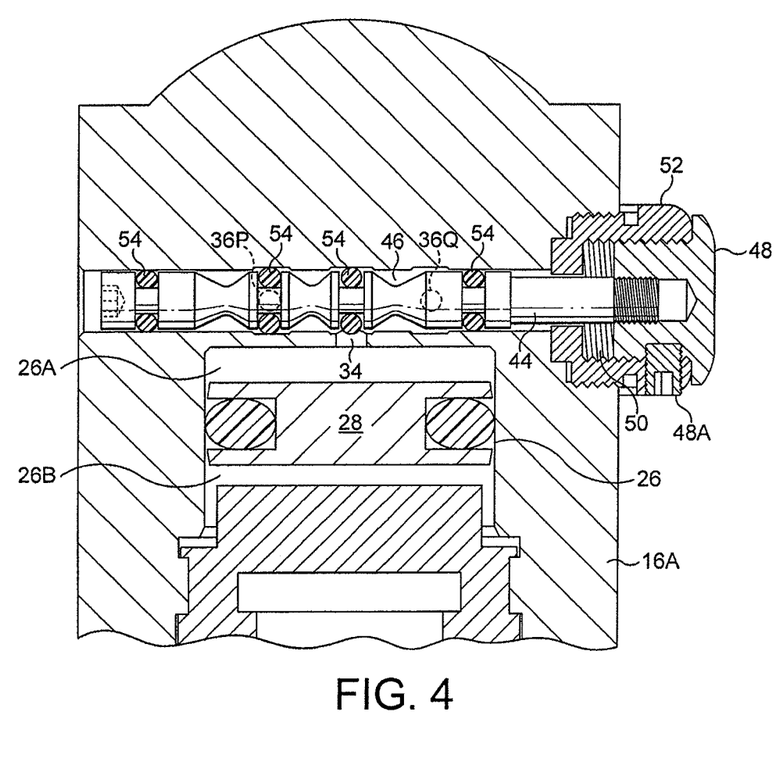
FIG. 4 is a detailed cross-section, taken on a medial-lateral plane, of the ankle unit of FIG. 2, showing a locking valve.

Referring now to FIG. 4, which is a partial cross-section of the ankle unit on a medial-lateral plane containing the axis of the locking valve 32, this locking valve is a spool valve having a spool member 44 which is slidable in a spool valve bore 46. The bore has three ports. A first port is that of the common linking passage 34 communicating with the upper chamber 26A of the cylinder 26. Second and third ports 36P, 36Q, offset medially and laterally with respect to the common passage 34, provide for communication with the bypass passages 36 (see FIG. 2).

At one end of the spool member 44, there is a manually operable pushbutton 48, which, when pushed against the outward biasing force of a stack 50 of spring washers encircling the spool member within a pushbutton housing 52, moves the spool member 44 to its open position, as shown in FIG. 4.

The spool valve bore 46 has three enlarged sections of increased diameter in registry, respectively, with the three ports described above. The spool member 44 has four full-diameter sections, with sealing rings 54, which are a sliding fit within the bore 46. When the spool member 44 is in its open position, as shown in FIG. 4, two of these full-diameter sections and their corresponding sealing rings 54 are in registry with the enlarged sections of the spool valve bore 46, thereby allowing fluid flow between the bypass passage ports 36P, 36Q and the common passage 34 communicating with the upper chamber 26A of the cylinder 26. Conversely, when the push button 48 is released, the spool member 44 moves to bring the above-mentioned full-diameter portions and their respective sealing rings 54 into registry with the non-enlarged sections of the spool valve bore 46 on each side of the port to the common passage 34, thereby preventing fluid flow between the upper cylinder chamber 26A and the bypass passage ports 36B, 36Q. It follows that when the pushbutton 48 is released, the ankle unit is hydraulically locked at whichever flexion angle existed at the moment of release. The pushbutton 48 has a projecting stud 48A which engages a detent recess in the push button housing 52 when the pushbutton is rotated, allowing the pushbutton to be maintained in its depressed position. This is the normal position of the spool valve, in which flow of hydraulic fluid through the bypass passages is 36 (FIG. 2) is allowed, with the result that the ankle unit allows yielding dorsi- and plantar-flexion.

The same locking valve arrangement is present in the ankle unit of the foot-ankle prosthesis described above with reference to FIG. 1.

Figure 5:
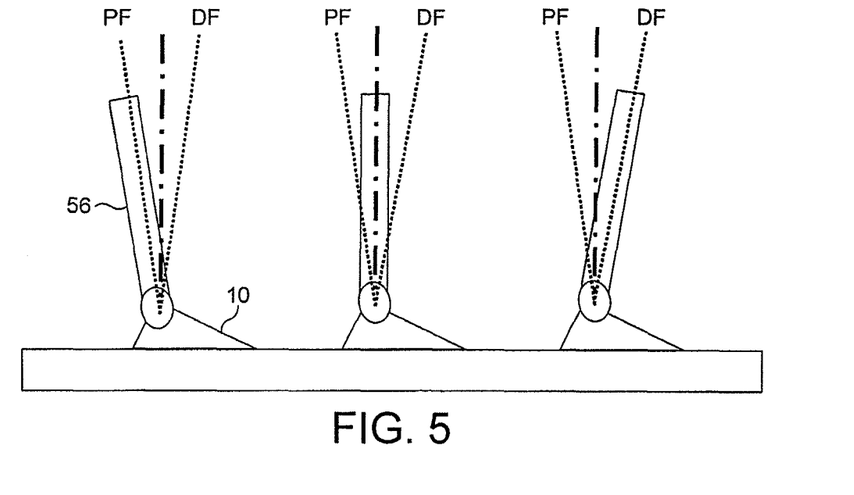
FIG. 5 is a diagram illustrating the ankle yielding range afforded by a prosthesis in accordance with the invention.

Whether the ankle unit is in the form of a two-part assembly for detachable mounting to a foot component, as described above with reference to FIGS. 2, 3 and 4, or in the form of an ankle unit directly pivotally mounted to a prosthetic foot, as described above with reference to FIG. 1, the joint mechanism allows yielding ankle flexion as shown diagrammatically in FIG. 5. The dotted lines denote plantar-flexion (PF) and dorsi-flexion (DF) limits of a mechanical hydraulic yielding range of flexion of a shin component 56 with respect to a foot component 10. The magnitude of the angular range is fixed by the geometry of the joint mechanism and its damping piston and cylinder assembly. Although in these preferred embodiments, the range magnitude is fixed, the position of the limits with respect to a neutral position indicated by the chain lines in FIG. 5 can be altered by adjusting the alignment of the shin component relative to the foot component using one of the alignable connection interfaces described above. In this way, the flexion range may be biased anteriorly or posteriorly from the position shown in FIG. 5 to create a larger range of motion in either the PF or DF direction. Typical alignment settings result in a dorsi-flexion limit at 2 degrees to 6 degrees tilt anteriorly with respect to the neutral axis, dependent on the foot toe spring stiffness in particular, and the plantar flexion limit at 4 degrees to 10 degrees tilt posteriorly with respect to the neutral axis (shown by the chain lines in FIG. 5).

Providing the manual hydraulic lock is not activated, the unit continuously allows yield in the dorsi direction (and plantar direction) up to the preset dorsi-flexion limit during walking and standing.

The applicants have found that providing a yielding ankle with minimal, preferably zero elastic biasing in the dorsi- or plantar directions, and with flexion limits set within the above ranges, provides advantages during stair walking and ramp walking activities, and during standing. In the normal body, the biomechanics of standing balance control are characterised by the natural balancing of external moments between joint centres of rotation. The geometrical position of the joint centres of rotations and the relative position of the body centre of gravity and the reaction vector are important for stabilising action. Limb stability with a prosthetic limb is primarily dependent on geometry, not muscle-induced internal moments. Consequently, standing can be achieved for long periods with minimal muscular effort. A small amount of cyclical postural sway of the upper body also helps to create stability. It follows that natural standing posture and balance control can be achieved with joints exhibiting low levels of internal resistive torque, the position of the ground reaction vector relative to the hip, knee and ankle joints being the main source of limb stability. Allowing yield in a prosthetic ankle in the manner provided by the ankle-foot prosthesis described above aids this function for a lower limb amputee.

Figure 6:
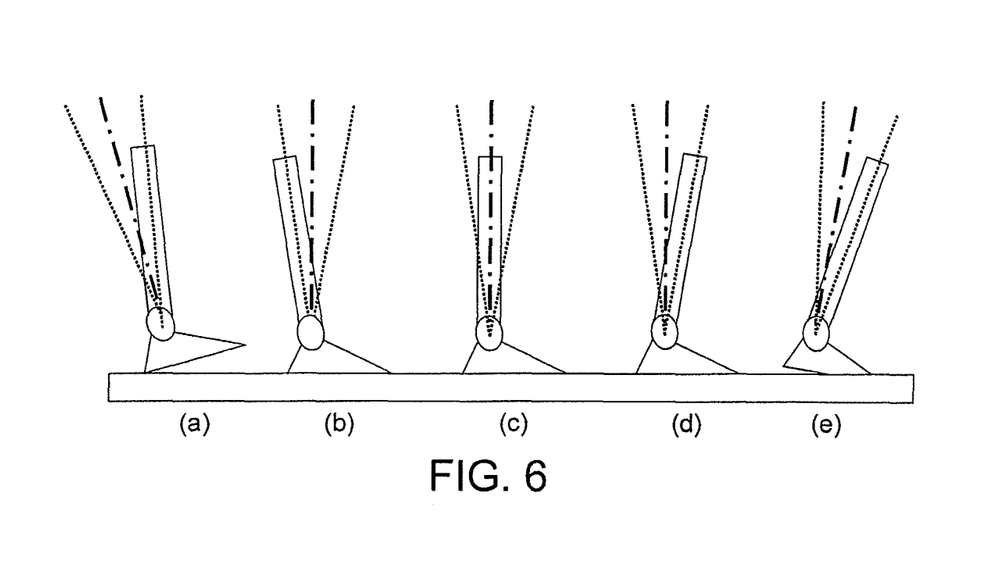
FIG. 6 is a diagram illustrating operation of a prosthesis in accordance with the invention during walking.

The dynamic action of a lower limb prosthesis having the features described above during the stance phase of walking is now described with reference to FIG. 6. At heel strike (a), the ankle is in a dorsi-flexed state from the roll-over actions of the previous step. As the foot moves towards the flat-foot state (b), the ankle plantar-flexes under the action of the foot heel spring and hydraulic yield at the ankle. In general, plantar-flexion at the ankle does not reach the plantar-flexion limit imposed by the joint mechanism of the prosthesis at this stage. During roll-over (c), the ankle begins to dorsi-flex by way of the hydraulic yield afforded by the prosthesis, providing a smooth roll-over action, preserving body momentum, and improving knee function. Towards the end of the roll-over phase (d), the dorsi-flexion limit imposed by the joint mechanism is reached. Once this happens, mechanical energy is directed into the keel of the foot (e) to provide energy return for push-off. The swing phase is initiated with the foot oriented at the dorsi-flexion end-stop to provide toe clearance during the swing phase.

In summary, the prosthesis described above is an foot-ankle system that is continuously allowed to yield over a limited range in plantar- and dorsi-flexion. The yielding action is provided by a hydraulic damper coupled to conventional foot elements (i.e. keel, carrier and independent carbon fibre composite heel-toe springs). The ankle is, therefore, free to flex continuously over a limited plantar- and dorsi-flexion range via the hydraulic damper with minimal interference from elastic elements during walking and standing. During standing, the relative positions of the hip, knee and ankle joint centres are such that substantially normal standing postures can be maintained, the moments about each joint being automatically balanced thereby creating limb stability. Moreover, the self-aligning action of the foot-ankle system facilitates improved control of energy transfer between limb segments during locomotion, the user's hip joint being the main driver and the knee joint being the main facilitator of mechanical energy transfer. This biomimetic method of stabilisation of standing stability and balance control has a further advantage in that, while standing on ramps, owing to the yielding action of the hydraulic components, there are no significant reaction moments generated around the ankle which may cause imbalance between joints and discomfort. Since, owing to the limited range of hydraulic yielding, the ankle is free to move, adaptation for walking and standing on inclined surfaces and changes to footwear with various heel heights is achieved automatically. A further advantage of the system is a smoother more progressive transition during roll-over over a variety of terrains.

Although a pneumatic piston and cylinder assembly can be used in place of a hydraulic one, the hydraulic variant is preferred, The preferred construction includes an alignment adaptor to allow setting and adjustment of the plantar-flexion and dorsi-flexion hydraulic yield limits. Such adjustment allows the prosthetist to provide for balancing of limb moments during standing.

The degree of resistance to flexion in the dorsi-direction or plantar-direction is manually adjustable (e.g. by rotation of flow control valve elements using a screwdriver). The control valves for controlling hydraulic resistance may, in an alternative embodiment, be replaced by a single adjustable control valve in a common bypass passage, supplemented, if necessary, by a second control valve in a branch passage.

In addition, the joint provided by the ankle-foot system may be hydraulically locked, preferably manually, but also, for instance, remotely in real time using an electrically controlled valve, preferably operated wirelessly via a key fob.

The dorsi-flexion end-stop may be cushioned, e.g. by inserting a compression spring on the upper cylinder wall or on the upper face of the piston. Alternatively, a resilient elastomeric or felt pad may be provided on one of these surfaces.

A further variation is the substitution of a hydraulic dorsi-flexion end stop in place of an end-stop determined by abutment of components of the joint mechanism. In this case the port via which the relevant bypass passage communicates with the chamber 26B (FIG. 2) of the piston and cylinder assembly may be located in the cylinder side wall of the cylinder above the lower wall of the lower chamber 26B so that as a piston 28 moves with dorsi-flexion of the mechanism, it covers the port thereby preventing further movement. The port may be shaped or divided into two or more openings into the chamber so that the resistance to dorsi-flexion increases as the dorsi-flexion limit is approached, providing a hydraulic cushion. A similar hydraulic stop may be provided by means of a port in the upper chamber 26A.

In summary, the preferred foot and ankle system as described has a linear piston arrangement for the simple control of a hydraulic damping range. There is no need for a pendulum as in some prior art arrangements, nor for electronic control at every step. The damping range is set mechanically, the linear piston arrangement being preferred for simplicity and reliability. Independent dorsi-flexion and plantar-flexion valve adjustment is provided, allowing improved setup and customisation of foot performance to suit the requirements of individual amputees. The preferred foot and ankle combination represents a visco-elastic structure according to the Maxwell model, i.e. the damper of the ankle joint mechanism acts in series with the resilient part of the foot. The hydraulic damping is active on a step-by-step basis, as opposed to being substantially locked on some steps.

What is claimed is:

1. A prosthetic foot and ankle assembly comprising a combination of:
   a foot component, and
   an ankle joint mounted to the foot component and having a fixed range of dorsi-plantar flexion during walking, the ankle joint comprising a joint mechanism providing resistance to ankle flexion, wherein the joint mechanism comprises:
      a hydraulic linear piston and cylinder assembly having a piston which is movable so as to define a pair of variable-volume chambers, one chamber located on each side of the piston and which is constructed and arranged to provide hydraulic damping continuously over the range of dorsi-plantar flexion, and
      a valve arrangement controlling the flow of hydraulic fluid between said chambers, the valve arrangement comprising first and second adjustable valves respectively comprising first and second orifices each adjustable in area for independently presetting dorsi-flexion damping resistance and plantar-flexion damping resistance respectively such that during walking said first orifice is preset to provide hydraulic damping at a first setting whenever the ankle joint is flexed in a dorsi-flexion direction and said second orifice is preset to provide hydraulic damping at a second setting whenever the ankle joint is flexed in a plantar-flexion direction,
   wherein the joint mechanism includes a first flexion limiter that limits dorsi-flexion of the joint mechanism to a dorsi-flexion limit and a second flexion limiter that limits plantar-flexion of the joint mechanism to a plantar-flexion limit, thereby defining said fixed range of dorsi-plantar flexion, the first and second flexion limiters comprising mechanical abutments of the joint mechanism.

2. A prosthetic foot and ankle assembly according to claim 1, having at least one pyramid alignment interface allowing adjustment of a shin axis orientation in an anterior-posterior direction with respect to the foot component.

3. A prosthetic foot and ankle assembly according to claim 1, wherein the joint mechanism defines a medial-lateral joint flexion axis, the linear piston and cylinder assembly has a central axis, and the medial-lateral joint flexion axis is located to an anterior of the central axis of the linear piston and cylinder assembly.

4. A prosthetic foot and ankle assembly according to claim 1, wherein said joint mechanism includes a first passage and a second passages, each passage being in communication with each of said chambers of the piston and cylinder assembly, said first passage containing said first adjustable valve and a first non-return valve and said second passage containing said second adjustable valve and a second non-return valve, said first non-return valve being oriented to prevent the flow of fluid between said chambers through said first passage in a first direction and said second non-return valve being oriented to prevent the flow of fluid between said chambers through said second passage in a second direction.

5. A prosthetic foot and ankle assembly according to claim 1, the assembly including a cushioning device for increasing resistance to dorsi-flexion as flexion of the ankle joint approaches said dorsi-flexion limit.

6. A prosthetic foot and ankle assembly according to claim 1, wherein the joint mechanism is non-electronically controlled and the hydraulic damping provided by the hydraulic linear piston and cylinder assembly is non-electronically controlled.

7. A prosthetic foot and ankle assembly according to claim 1, wherein the joint mechanism is constructed and arranged such that during walking said resistance to ankle flexion is predominantly provided by hydraulic damping in one or both of the dorsi- and plantar-flexion directions.

8. A prosthetic foot and ankle assembly comprising a combination of:
   a foot component, and
   an ankle joint mounted to the foot component and having a fixed range of dorsi-plantar flexion, the ankle joint comprising a joint mechanism providing resistance to ankle flexion, wherein the joint mechanism comprises:
      a hydraulic linear piston and cylinder assembly having a cylinder and a piston, the chamber having a pair of end walls and the piston being movable between the end walls so as to define a pair of variable-volume chambers, one chamber located on each side of the piston and which is constructed and arranged to provide hydraulic damping continuously over the range of dorsi-plantar flexion, and
      a valve arrangement controlling the flow of hydraulic fluid between said chambers, the valve arrangement comprising first and second adjustable valves respectively comprising first and second orifices each adjustable in area for independently presetting dorsi-flexion damping resistance and plantar-flexion damping resistance respectively such that said first orifice is preset to provide hydraulic damping at a first setting whenever the ankle joint is flexed in a dorsi-flexion direction and said second orifice is preset to provide hydraulic damping at a second setting whenever the ankle joint is flexed in a plantar-flexion direction,
   wherein the joint mechanism includes a flexion limiter that limits dorsi-flexion of the joint mechanism to a dorsi-flexion limit, the flexion limiter comprising a resilient elastomeric pad on a chamber end wall or on a face of the piston.

9. A prosthetic foot and ankle assembly comprising a combination of:
   a foot component, and
   an ankle joint pivotally mounted to the foot component at a first pivotal connection and having a fixed range of dorsi-plantar flexion about the first pivotal connection, the ankle joint having a pyramid alignment interface for connection to a shin component defining a shin axis and for allowing adjustment of an orientation of the shin axis in an anterior-posterior direction with respect to the foot component, the ankle joint comprising a joint mechanism providing resistance to ankle flexion, wherein the joint mechanism comprises:
      a hydraulic linear piston and cylinder assembly having a piston which is movable so as to define a pair of variable-volume chambers, one chamber located on each side of the piston and which is constructed and arranged to provide hydraulic damping continuously over the range of dorsi-plantar flexion, and
      a valve arrangement controlling the flow of hydraulic fluid between said chambers, the valve arrangement comprising first and second adjustable valves respectively comprising first and a second orifices each adjustable in area for independently presetting dorsi-flexion damping resistance and plantar-flexion damping resistance respectively such that said first orifice is preset to provide hydraulic damping at a first setting whenever the ankle joint is flexed in a dorsi-flexion direction and said second orifice is preset to provide hydraulic damping at a second setting whenever the ankle joint is flexed in a plantar-flexion direction, wherein the pyramid alignment interface has a central axis which is substantially aligned with the central axis of the linear piston and cylinder assembly, and the linear piston and cylinder assembly is pivotally connected to the foot component at a second pivotal connection displaced in an anterior-posterior direction from the first pivotal connection such that pivotal motion of the foot component relative to the ankle joint about the first pivotal connection causes the piston to move in the cylinder so as to provide hydraulic damping of ankle flexion.

* * * * *